(12) United States Patent
Sreenivasan et al.

(10) Patent No.: US 11,056,227 B2
(45) Date of Patent: Jul. 6, 2021

(54) SYSTEM AND METHOD FOR GENERATING TEXTUAL DESCRIPTIONS FROM MEDICAL IMAGES

(71) Applicant: KONINKLIJKE PHILIPS N.V., Eindhoven (NL)

(72) Inventors: Rithesh Sreenivasan, Bangalore (IN); Shreya Anand, Bangalore (IN); Tilak Raj Arora, Haryana (IN); Oladimeji Feyisetan Farri, Yorktown Heights, NY (US); Sheikh Sadid Al Hasan, Cambridge, MA (US); Yuan Ling, Somerville, MA (US); Junyi Liu, Windham, NH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 184 days.

(21) Appl. No.: 15/987,164

(22) Filed: May 23, 2018

(65) Prior Publication Data

US 2019/0362835 A1 Nov. 28, 2019

(51) Int. Cl.
*G16H 30/40* (2018.01)
*G16H 15/00* (2018.01)
(Continued)

(52) U.S. Cl.
CPC .............. *G16H 30/40* (2018.01); *G06N 20/00* (2019.01); *G06T 7/0012* (2013.01); *G16H 15/00* (2018.01);
(Continued)

(58) Field of Classification Search
CPC ........ G16H 15/00; G16H 30/20; G16H 10/40; G16H 10/60; G16H 40/20; G16H 80/00;
(Continued)

(56) References Cited

U.S. PATENT DOCUMENTS

2007/0036402 A1* 2/2007 Cahill .................. G06T 7/0012
382/128
2008/0273774 A1* 11/2008 Mikhail ................ G16H 30/40
382/128
(Continued)

OTHER PUBLICATIONS

Simonyan, et al: "Very Deep Convolutional Networks for Large-Scale Image Recognition", ICLR 2015.
(Continued)

*Primary Examiner* — Ajibola A Akinyemi

(57) ABSTRACT

A method for generating a textual description from a medical image, comprising: receiving a medical image having a first modality to a system configured to generate a textual description of the medical image; determining, using an imaging modality classification module, that the first modality is a specific one of a plurality of different modalities; determining, using an anatomy classification module, that the medical image comprises information about a specific portion of an anatomy; identifying, by an orchestrator module based at least on the determined first modality, which of a plurality of different text generation models to utilize to generate a textual description from the medical image; generating, by a text generation module utilizing the identified text generation model, a textual description from the medical image; and reporting, via a user interface of the system, the generated textual description.

20 Claims, 6 Drawing Sheets

(51) Int. Cl.
*G06T 7/00* (2017.01)
*G06N 20/00* (2019.01)

(52) U.S. Cl.
CPC ............... *G06T 2207/10081* (2013.01); *G06T 2207/10088* (2013.01); *G06T 2207/10104* (2013.01); *G06T 2207/10116* (2013.01)

(58) Field of Classification Search
CPC ........ G16H 50/20; G16H 30/40; G16H 50/70; G16H 70/00; G16H 70/60; G16H 10/65; G16H 70/20; G16H 20/00; G16H 40/63; G16H 50/50; G16H 20/10; G16H 20/70; G16H 20/90
USPC .......................................................... 382/131
See application file for complete search history.

(56) References Cited

U.S. PATENT DOCUMENTS

| | | | | |
|---|---|---|---|---|
| 2010/0145720 | A1* | 6/2010 | Reiner | G16H 50/20 |
| | | | | 705/2 |
| 2019/0180861 | A1* | 6/2019 | Reicher | G16H 40/67 |

OTHER PUBLICATIONS

Xu, et al: "Show, Attend and Tell: Neural Image Caption Generation with Visual Attention", Cornell University, 2015.

* cited by examiner

SYSTEM AND METHOD FOR GENERATING TEXTUAL DESCRIPTIONS FROM MEDICAL IMAGES

FIELD OF THE DISCLOSURE

The present disclosure is directed generally to methods and systems for automated generation of a textual description from a medical image.

BACKGROUND

Medical images are utilized for the diagnosis and treatment of a wide array of conditions and diseases. CT scans, MRIs, X-rays, and ultrasound images are just a few of the medical imaging techniques used for diagnosis and treatment. Typically, radiologists perform specific steps to acquire a medical image, interpret it, and then prepare a report for the clinician. As a result, the knowledge, skills, and experience of a radiologist all play a vital role in medical image interpretation.

Since there are many forms and methods for medical imaging, significant time and experience is required to understand a medical image. Novice radiologists may lack this experience or may be trained in modern imaging techniques that hinder their ability to interpret medical images generated using older imaging techniques. Additionally, experienced radiologists may not be properly trained for the latest imaging techniques, and thus it may be difficult for experienced radiologists to understand the information present in a medial image. Moreover, current visual evaluations and interpretations are not always effective. A radiologist at any experience level may encounter difficulties that place a significant burden on the overall workflow across the care continuum. Indeed, interpreting medical images and summarizing the information contained therein in a text format is an intensely time-consuming task that often represents a bottleneck in clinical diagnosis pipelines.

SUMMARY OF THE EMBODIMENTS

There is a continued need for automated systems and methods that can generate a textual description of a medical image, thereby eliminating bottlenecks and improving patient care.

The present disclosure is directed to inventive methods and systems for the automated generation of textual descriptions from medical images which are generated from various different imaging modalities. Various embodiments and implementations herein are directed to a textual description generation system that utilizes one or more classifiers to characterize a medical image. Upon receiving a medical image captured using an imaging modality, a trained imaging modality classifier of the system analyzes the medical image to determine what imaging modality was utilized. Similarly, a trained anatomy classifier of the system analyzes the medical image to determine what anatomy or anatomies are represented in the image. Based on the determined imaging modality, a orchestrator module of the system determines which of a plurality of different text generation models to utilize to generate a textual description from the medical image, where different text generation models are utilized for different modalities. Lastly, a text generation module of the system uses the identified text generation model to generate the textual description from the medical image. The system reports the generated textual description to a clinician via a user interface, where it can be utilized for patient care.

Generally in one aspect, a method for generating a textual description from a medical image is provided. The method includes: (i) receiving a medical image having a first modality to a system configured to generate a textual description of the medical image; (ii) determining, using an imaging modality classification module of the system, that the first modality is a specific one of a plurality of different modalities, wherein the imaging modality classification module is trained to differentiate between the plurality of different modalities; (iii) determining, using an anatomy classification module of the system, that the medical image comprises information about a specific portion of an anatomy, wherein the anatomy classification module is trained to differentiate between specific portions of anatomy; (iv) identifying, by an orchestrator module of the system based at least on the determined first modality, which of a plurality of different text generation models to utilize to generate a textual description from the medical image, wherein each of the plurality of different text generation models is utilized for a different modality; (v) generating, by a text generation module of the system utilizing the identified text generation model, a textual description from the medical image, wherein the text generation module is trained to generate the textual description based at least in part on information from the medical image; and (vi) reporting, via a user interface of the system, the generated textual description.

According to an embodiment, the method further includes the step of training, using a training data set comprising a plurality of medical images obtained using different imaging modalities, the imaging modality classification module to differentiate between a plurality of different imaging modalities.

According to an embodiment, the plurality of different imaging modalities comprises at least CT scan, X-ray, MRI, PET scan, and ultrasound.

According to an embodiment, the method further includes the step of training, using a training data set, the anatomy classification module to differentiate between a plurality of portions of anatomy.

According to an embodiment, the method further includes the step of utilizing the reported textual description for diagnosis or treatment.

According to an embodiment, the orchestrator module is configured to receive the medical image, and further configured to communicate the medical image to one or more of the imaging modality classification module, the anatomy classification module, and the text generation module.

According to an embodiment, the step of reporting the generated textual description comprises providing both the generated textual description and displaying the medical image.

According to an embodiment, one or more of the imaging modality classification module, the anatomy classification module, and the text generation module comprises a machine learning algorithm.

In one aspect, a system for generating a textual description from a medical image is provided. The system includes: (i) an imaging modality classification module configured to receive a first medical image of a first image modality, and further configured to determine that the first modality is a specific one of a plurality of different modalities, wherein the imaging modality classification module is trained to differentiate between the plurality of different modalities; (ii) an anatomy classification module configured to determine an anatomy represented in the medical image, wherein the anatomy classification module is trained to differentiate between different anatomy in medical images; (iii) an orchestrator module configured to determine, based at least on the determined first modality, which of a plurality of different text generation models to utilize to generate a textual description from the medical image, wherein each of the plurality of different text generation models is utilized for a different modality; (iv) a text generation module configured to generate, utilizing the identified text generation model, a textual description from the medical image, wherein the text generation module is trained to generate the textual description based at least in part on information from the medical image; and (v) a user interface configured to report the generated textual description.

According to an embodiment, the system further includes imaging hardware configured to obtain the medical image using the first modality.

According to an embodiment, the orchestrator module is configured to receive the medical image, and further configured to communicate the medical image to one or more of the imaging modality classification module, the anatomy classification module, and the text generation module.

According to an embodiment, the user interface is configured to report the generated textual description and to display the medical image. According to an embodiment, the user interface is configured to report the generated textual description to a clinician for diagnosis or treatment.

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the various embodiments discussed herein. The terms "program" or "computer program" are used herein in a generic sense to refer to any type of computer code (e.g., software or microcode) that can be employed to program one or more processors or controllers.

The term "network" as used herein refers to any interconnection of two or more devices (including controllers or processors) that facilitates the transport of information (e.g. for device control, data storage, data exchange, etc.) between any two or more devices and/or among multiple devices coupled to the network. As should be readily appreciated, various implementations of networks suitable for interconnecting multiple devices may include any of a variety of network topologies and employ any of a variety of communication protocols. Additionally, in various networks according to the present disclosure, any one connection between two devices may represent a dedicated connection between the two systems, or alternatively a non-dedicated connection. In addition to carrying information intended for the two devices, such a non-dedicated connection may carry information not necessarily intended for either of the two devices (e.g., an open network connection). Furthermore, it should be readily appreciated that various networks of devices as discussed herein may employ one or more wireless, wire/cable, and/or fiber optic links to facilitate information transport throughout the network.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

DETAILED DESCRIPTION OF EMBODIMENTS

The present disclosure describes various embodiments of a system for generating a textual description of an image. More generally, Applicant has recognized and appreciated that it would be beneficial to provide an automated system to interpret medical images. The system uses a trained imaging modality classifier to determine which of a plurality of possible imaging modalities was utilized to capture a medical image provided to the system. A trained anatomy classifier analyzes the medical image to determine what anatomy or anatomies are represented in the image. Based on the determined imaging modality, the system determines which of a plurality of possible text generation models to utilize to generate a textual description from the medical image. A text generation module of the system uses the identified text generation model to generate the textual description from the medical image. The system reports the generated textual description to a clinician via a user interface, where it can be utilized for patient care. According to an embodiment, the system uses deep-learning techniques or other machine learning processes to map visual information to condensed textual descriptions.

Figure 1:
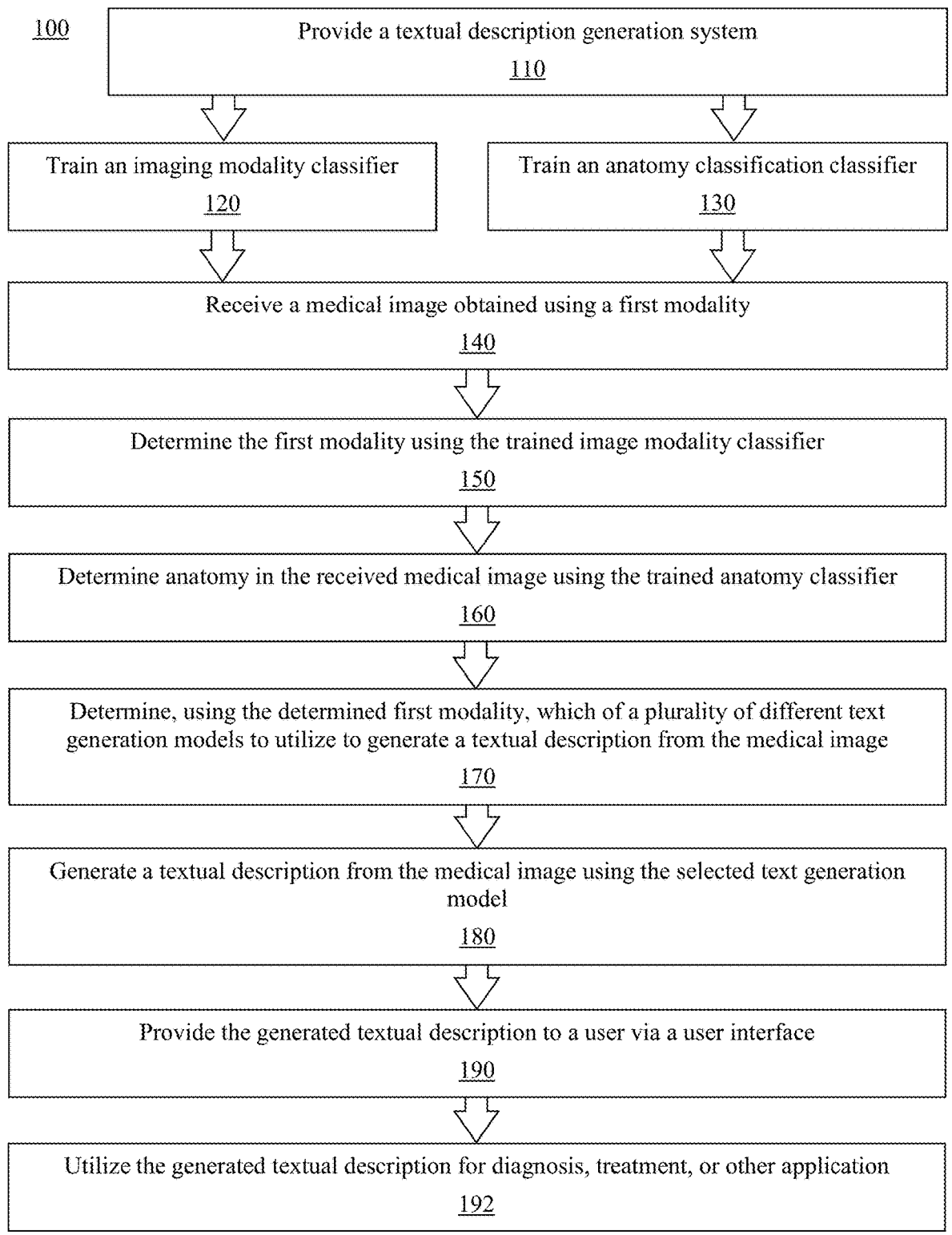
FIG. 1 is a flowchart of a method for generating a textual description of a medical image, in accordance with an embodiment.
Figure 2:
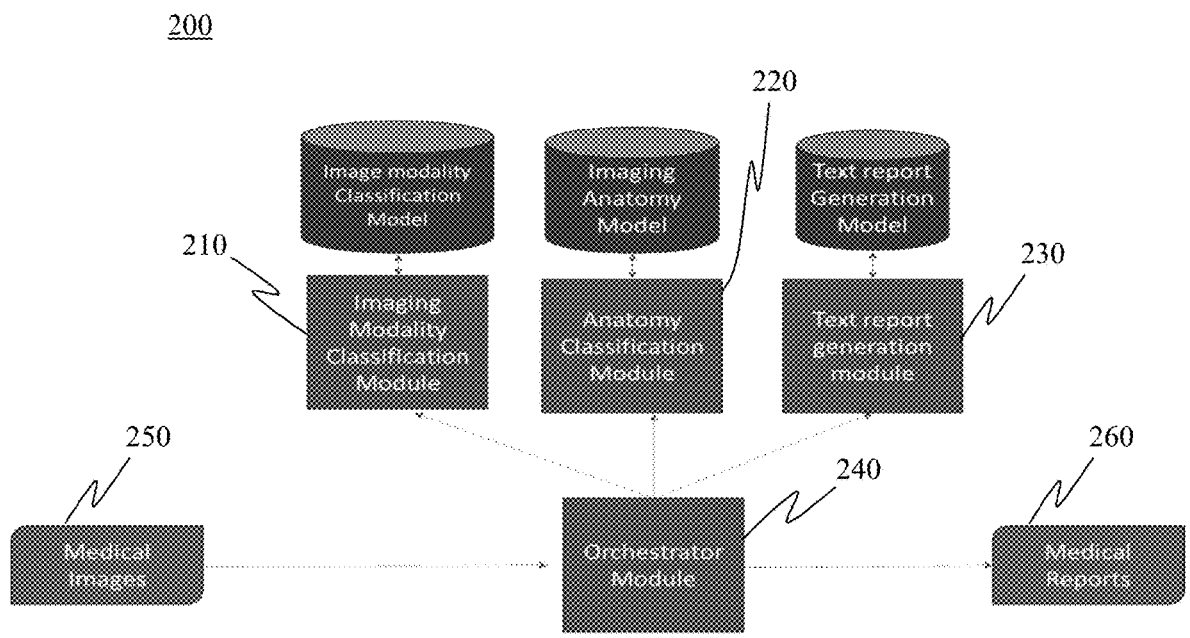
FIG. 2 is a schematic representation of a system for generating a textual description of a medical image, in accordance with an embodiment.

Referring to FIG. 1, in one embodiment, is a flowchart of a method 100 for generating a textual description of a medical image. At step 110 of the method a textual description generation system is provided. The textual description generation system may be any of the systems described or otherwise envisioned herein. For example, the textual description generation system can comprise a processor having or in communication with an image modality classification module configured or programmed to differentiate between a plurality of different imaging modalities, an anatomy classification module configured or programmed to differentiate between specific portions of anatomy in an image, a text report generation module configured or programmed to generate a textual description based at least in part on information from a medical image, and/or an orchestrator module configured or programmed to transmit and/or receive data between the modules and to determine which of a plurality of different text generation models to utilize to generate a textual description from the medical image. Many other systems, modules, and components are possible. Referring to FIG. 2, in one embodiment, is a schematic representation of a system 200 comprising an image modality classification module 210, an anatomy classification module 220, a text report generation module 230, and an orchestrator module 240. The orchestrator module 240 receives one or more medical images 250 and provides as output one or more medical reports 260 comprising textual descriptions of the one or more medical images.

At step 120 of the method, the system is trained to differentiate between a plurality of different imaging modalities. According to an embodiment, the system comprises an image modality classifier trained to utilize one or more parameters, features, or other aspects of an image to determine the imaging modality utilized to obtain the image. The system may process an image and utilize any information from that image to determine the imaging modality utilized to obtain the image. According to an embodiment, the system comprises an image modality classification module trained using a data set comprising a plurality of medical images obtained using different imaging modalities including but not limited to least photographs, CT scans, X-rays, MRIs, PET scans, ultrasound, and many other imaging modalities. The image modality classifier can be trained using any method or model for training, including but not limited to a machine learning approach, among others.

According to an embodiment, the image modality classifier—and any other classifiers described or otherwise envisioned herein—may be trained with adaptive learning rate algorithms, such as Adam, which uses stochastic gradient decent (i.e., an algorithm for first-order gradient-based optimization of stochastic objective functions) based on adaptive estimates of lower order moments, and regularization mechanisms such as dropout, among many other methods. For example, a very deep convolutional neural network architecture may be used by the image modality classifier to identify the imaging modality source. Additionally, the network architecture may be modified by including an additional softmax layer at the end for classifying medical images into N imaging modality classes. Many other methods are possible.

The image modality classifier can be trained and tested until a certain level of proficiency is obtained, which can be determined by a designer or a user of the system. For example, the image modality classifier can be tested using known data, other than the training data set, to evaluate an accuracy rate for which image modality is properly identified by the classifier.

Figure 3:
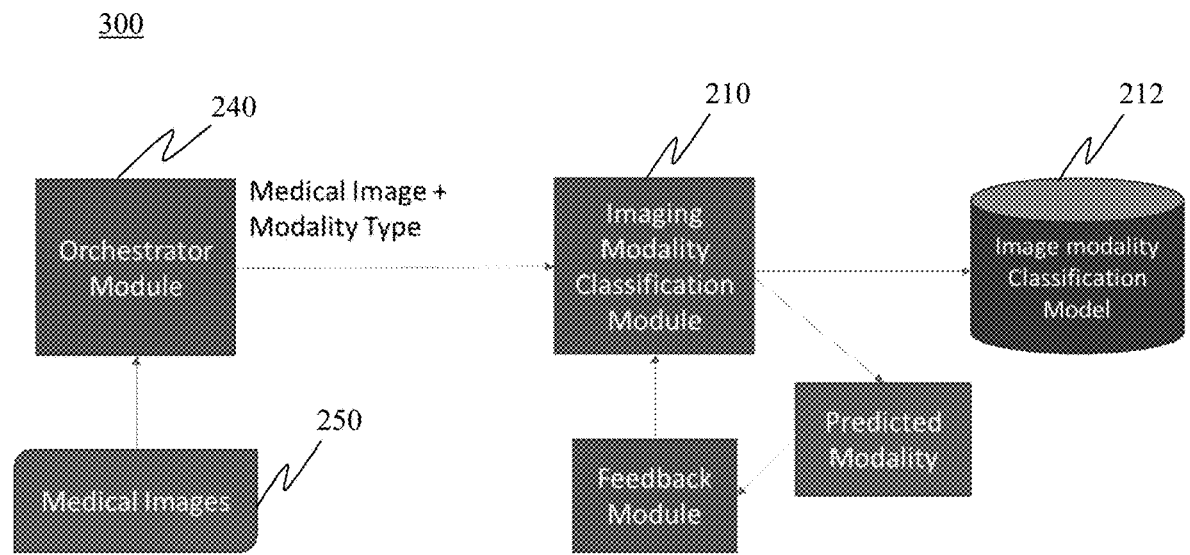
FIG. 3 is a schematic representation of a system for classifying the modality of a medical image, in accordance with an embodiment.

Referring to FIG. 3, in one embodiment, is a schematic representation of a system 300 comprising an image modality classification module 210 configured to determine the imaging modality utilized to obtain medical image 250. According to an embodiment, image modality classification module 210 receives image data from the orchestrator module 240 and utilizes an image modality classification model 212 to analyze that image data and predict or determine the image modality.

At step 130 of the method, the system is trained to differentiate between a plurality of different portions of anatomy. According to an embodiment, the system comprises an anatomy classifier trained to utilize one or more parameters, features, or other aspects of an image to determine the anatomy contained within the image. The system may process an image and utilize any information from that image to determine the anatomy, anatomies, or structures contained within the image. According to an embodiment, the system comprises an anatomy classification module trained using a data set comprising a plurality of medical images of a plurality of different anatomies. The anatomy classifier can be trained using any method or model for training, including but not limited to a machine learning approach, among others.

The anatomy classifier can be trained and tested until a certain level of proficiency is obtained, which can be determined by a designer or a user of the system. For example, the anatomy classifier can be tested using known data, other than the training data set, to evaluate an accuracy rate for which anatomy is properly identified by the classifier.

Figure 4:
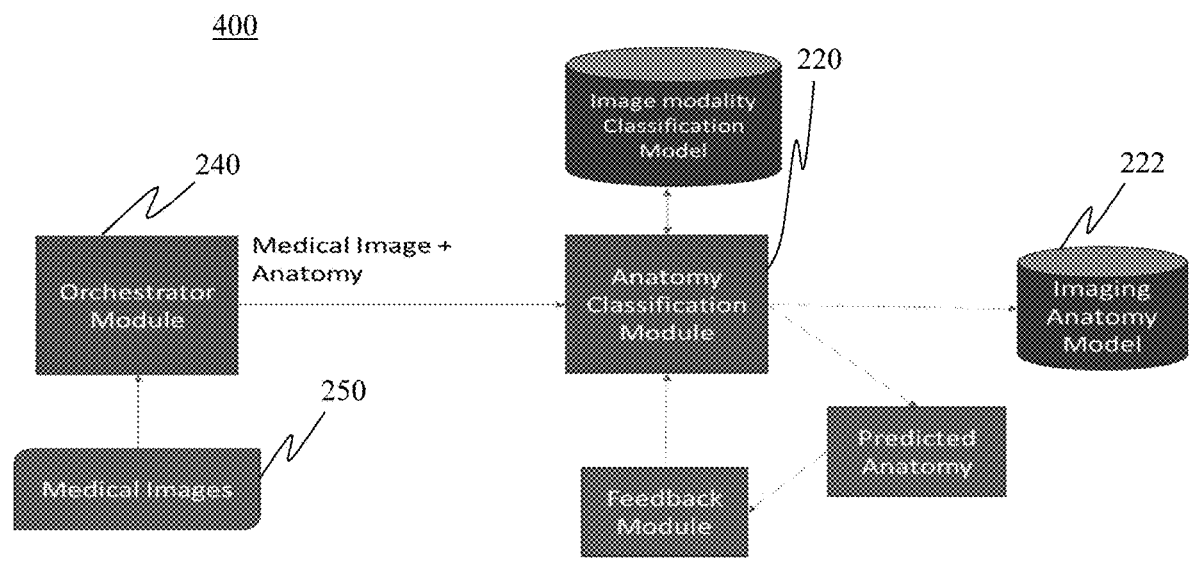
FIG. 4 is a schematic representation of a system for classifying the anatomy of a medical image, in accordance with an embodiment.

Referring to FIG. 4, in one embodiment, is a schematic representation of a system 400 comprising an anatomy classification module 220 configured to determine the anatomy or structure contained with a medical image 250. According to an embodiment, anatomy classification module 220 receives image data from the orchestrator module 240 and utilizes an anatomy model 222 to analyze that image data and predict or determine the anatomy or structure contained with the image.

Steps 120 and 130 may be performed simultaneously or contemporaneously, or may be performed at different times and/or locations. For example, the image modality classifier and the anatomy classifier may be trained using the same training data at the same time, using the same training data at different times, and/or using different training data. According to one embodiment, the image modality classifier and the anatomy classifier are trained by a developer of the text generation system prior to implementation of the system in a clinical setting.

The system may undergo additional training as well. For example, during the training of the system, the descriptions and/or captions associated with the medical images may be semantically preprocessed via a clinical ontology. The model also may be trained using images associated with their clinical concepts and later during a testing or deployment phase the generated concepts may be replaced with clinical ontology terms to provide more context to the generated textual descriptions.

At step 140 of the method, the system receives a medical image obtained using a first imaging modality. For example, the medical image may be obtained by standard photography, CT scan, X-ray, MRI, PET scan, ultrasound, and/or many other imaging modalities. Typically, the medical image will be provided in a digital format, or will be converted from an analog or other non-digital format to a digital format. The medical image may be obtained by the system directly, or may be provided to the system from an external source. For example, a facility or other clinical setting or network may comprise one or more text generation systems configured to receive medical images from a variety of different providers, internally and/or externally. Accordingly, the text generation system may receive X-rays from a first device or facility, and may receive MRI images from a second device or facility. Alternatively, the text generation system may receive all medical images from the same device or facility. As another option, the text generation system may receive medical images that are uploaded or downloaded to the system or are otherwise directly provided by a clinician, technician, or other provider. The text generation system may receive a medical image directly from the modality by which the image is obtained, and thus the text generation system may comprise or be in communication with a wired and/or wireless communications network configured to receive these medical images.

At step 150 of the method, the trained image modality classifier determines which imaging modality was utilized to obtain the received medical image. As described herein, the image modality classifier can be trained to analyze the received medical image to distinguish between standard photography, CT scan, X-ray, MRI, PET scan, ultrasound, and/or many other imaging modalities. According to an embodiment, a trained imaging modality classification module of the text generation system analyzes one or more parameters, features, or other aspects of the received medical image to determine which imaging modality was utilized to obtain the received medical image. The trained imaging modality classification module may comprise or utilize any machine learning algorithm or method for analysis of the image, including but not limited to a very deep convolutional neural network architecture among others.

At step 160 of the method, the trained anatomy classifier determines which anatomy or structures are present in the received medical image. As described herein, the anatomy classifier can be trained to analyze the received medical image to distinguish between different anatomy, anatomies, or structures in medical images. This may depend upon, for example, the organism from which the images may be obtained. In addition to human anatomy, the system may be configured to analyze images obtained from animals for diagnosis, treatment, and other clinical purposes. According to an embodiment, a trained anatomy classification module of the text generation system analyzes one or more parameters, features, or other aspects of the received medical image to determine which anatomy is partially and/or completely contained within or otherwise represented by the image.

As just one example, if the received medical image is an MRI image of a portion or slice of an individual's brain, the anatomy classification module of the text generation system analyzes the image and determines that the image comprises brain and/or one or more regions of the brain. According to an embodiment, the pre-trained convolution neural network employed by the anatomy classification module may be similar to the convolution neural network employed in the imaging modality classification module and/or the convolution neural network employed by the anatomy classification module may include a last softmax layer with the dimensionality as the number of anatomy regions per imaging modality. Many other methods are possible.

Following steps 150 and 160 of the method, the text generation system has identified the most likely imaging modality utilized to obtain the received medical image, as well as the anatomy most likely contained within or represented by the received medical image. The text generation system can then utilize this information in downstream steps of the method. The information can be stored in memory or otherwise associated with the medical image, and/or can be reported to a user of the system via a user interface or other reporting mechanism.

At step 170 of the method the text generation system determines, based at least in part on the determined image modality for the received medical image, which of a plurality of different text generation models to utilize to generate a textual description from the medical image. According to an embodiment, the system comprises a plurality of different text generation models each of which may function more efficiently and/or with higher accuracy for a specific image modality. For example, a first text generation model may function best for X-ray images, and a second text generation model may function best for MRI images. As another example, a text generation model may function best for several different image modalities, but may not function well for other image modalities. Accordingly, the text generation system can be configured to select one or more of these models based on the determined image modality. For example, the system may comprise a table linking certain models with certain image modalities, and/or an algorithm configured to select a text generation model based on the determined image modality.

According to an embodiment, the text generation system comprises an orchestrator module configured to select or determine, based at least in part on the determined image modality, which of the plurality of different text generation modules to utilize to generate a textual description from the medical image. According to an embodiment, the orchestrator module facilitates text report generation from a medical image. For example, the orchestrator module may process data during classifier training and thus may receive as input a set of medical images of various modalities along with associated text reports. The orchestrator module may take, as an input, a list of imaging modalities and associated anatomies. The orchestrator module may then set up the initial configuration for the various modules during the training process. In a testing phase, the orchestrator module may take as input either a medical image or set of medical images and apply an appropriate modality- and anatomy-focused model at each of the modules to generate a text report.

Figure 5:
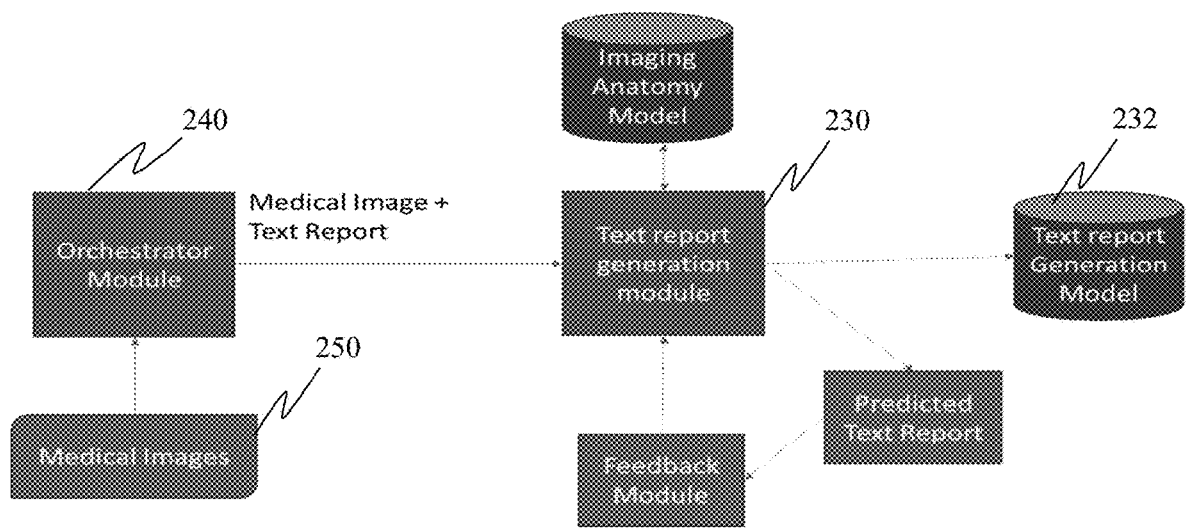
FIG. 5 is a schematic representation of a system for generating a textual description of a medical image, in accordance with an embodiment.

Referring to FIG. 5, in one embodiment, is a schematic representation of a system 500 comprising a text generation module 230. According to an embodiment, text generation module 230 receives image data from the orchestrator module 240 and utilizes a text generation model 232, which may be one of several models, to analyze that image data and generate a textual description of the image.

Figure 6:
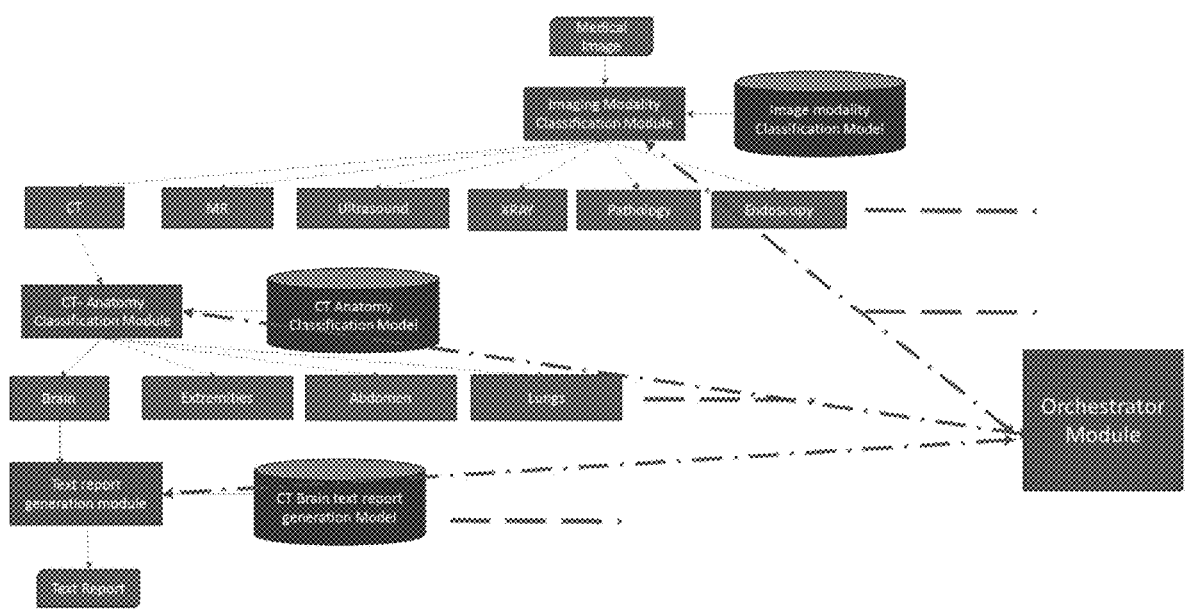
FIG. 6 is a schematic representation of a system for generating a textual description of a medical image with illustrative examples, in accordance with an embodiment.

Referring to FIG. 6, in one embodiment, is a schematic representation of a system 600 comprising an image modality classification module having one or more image modality classification models, an anatomy classification module having one or more anatomy classification models, a text report generation module having one or more text generation models, and an orchestrator module. The orchestrator module receives one or more medical images and provides as output one or more medical reports comprising textual descriptions of the one or more medical images.

At step 180 of the method, a text generation module of the text generation system utilizes the selected text generation model to generate a textual description from the medical image. According to an embodiment, the text generation model is trained to generate the textual description based at least in part on information from the medical image. The text generation model may be any model configured or programmed to generate a textual description from a medical image.

According to one embodiment, the text generation module comprising one or more text generation models may utilize a combination of convolutional neural network and recurrent neural network architectures, among other models. This model may use an encoder-decoder architecture where the encoder encodes an image into a fixed length feature representation and the decoder decodes the representation to a sequence of words using an attention-based mechanism. For example, the encoder may use a deep convolutional neural network to encode a raw medical image to a feature representation, which may be in turn decoded using an attention-based recurrent neural network to generate a most relevant caption for a given image. A decoder may use a long short-term memory network with a soft attention mechanism to generate a caption by predicting one word at every time step based on a context vector (which represents the important portions of an image to focus on), the previous hidden state, and the previously generated words. The attention method may automatically learn to emphasize on salient parts of the image while generating corresponding words in the output sentences. Many other methods for generating the textual description utilizing a text generation model are possible.

At step 190 of the method, the text generation system reports the generated textual description to a user via a user interface of the system. The generated textual description may be provided in any format to the user, who may be a technician, clinician, or other user of the system. For example, the generated textual description may be provided via a printed report, visual display, vocalization, digital download or upload, and/or via any other method of information communication. Accordingly, the user interface may comprise any component or method for information transmission, including but not limited to a printer, display, speaker, and/or any other component or element. The generated textual description may be provided together with other information such as the received medical image, metadata about the patient and/or the medical image, and/or any other information.

As an additional step 192 of the method, a technician, clinician, or other user receiving the generated textual description utilizes the description to inform a diagnosis, treatment, and/or any other aspect of medical diagnosis, care, or treatment. For example, a technician receiving the generated textual description can utilize the information to supplement or replace a visual inspection of the medical image. A clinician receiving the generated textual description can utilize the information to make or supplement a diagnosis or other clinical analysis, and/or can utilize the information to make or supplement a course of treatment for a patient.

As just one example, the text generation system may receive an X-ray image of a patient's arm, which is transferred directly via communications network from an X-ray machine in a hospital or care facility to the local or remote text generation system. The image modality classifier processes and/or analyzes the received medical image and determines that the image modality is X-ray. The anatomy classifier processes and/or analyzes the received medical image and determines that the image comprises the elbow region of a right arm, including a lower portion of a humerus and the upper portions of a radius and ulna. Based on the determination by the image modality classifier that the modality is X-ray, the orchestrator module selects a text generation model that works best for X-ray images. The text generation module processes and/or analyzes the received medical image utilizing the selected text generation model and generates text that summarizes or otherwise describes the medical image. In this example, the selected text generation model describes an oblique fracture of the lower humerus.

As just one example, the text generation system may receive an MRI image of a portion of a patient's brain, which is transferred directly via communications network from an MRI machine in a hospital or care facility to the local or remote text generation system. The image modality classifier processes and/or analyzes the received medical image and determines that the image modality is MRI. The anatomy classifier processes and/or analyzes the received medical image and determines that the image comprises a hypothalamus of a human brain. Based on the determination by the image modality classifier that the modality is MRI, the orchestrator module selects a text generation model that works best for MRI images. The text generation module processes and/or analyzes the received medical image utilizing the selected text generation model and generates text that summarizes or otherwise describes the medical image. In this example, the selected text generation model describes a hamartoma in the tuber cinereum of the hypothalamus, comprising certain dimensions.

By way of example, a method using at least one of the modules described or otherwise envisioned herein may include no sematic pre-processing of captions, whereby the entire training and validation set are used to train the model. A method using at least one of the modules described herein may consider sematic pre-processing of captions using MetaMap and the Unified Medical Language System (UMLS) metathesaurus, initially trained on a modified pre-trained CNN model with a randomly selected subset of training images to automatically generate image features and classified the imaging modality, and then finally trained as described herein with a random subset of training images and validation images to minimize time and computational complexity. A method using at least one of the modules described herein may include an automatic generation of UMLS concept unique identifiers (CUIs) using a training dataset for the concept detection task, instead of captions from the caption prediction task, and then replacing the CUIs (generated for the test set) with the longest relevant clinical terms from the UMLS metathesaurus as the caption. A method using at least one of the modules described herein may replace the CUIs (generated for the test set) with all relevant clinical terms (including synonyms) from the UMLS metathesaurus as the caption.

For concept detection tasks using the modules describe herein, a method may include considering the task as a sequence-to-sequence generate problem, where the CUIs associated with an image are treated as a sequence of concepts and the entire training and validation set are used to train the module(s) as described herein. A concept detection task method also may include transforming the generated image descriptions by replacing clinical terms with a best possible CUI(s) from the UMLS metathesaurus.

Figure 7:
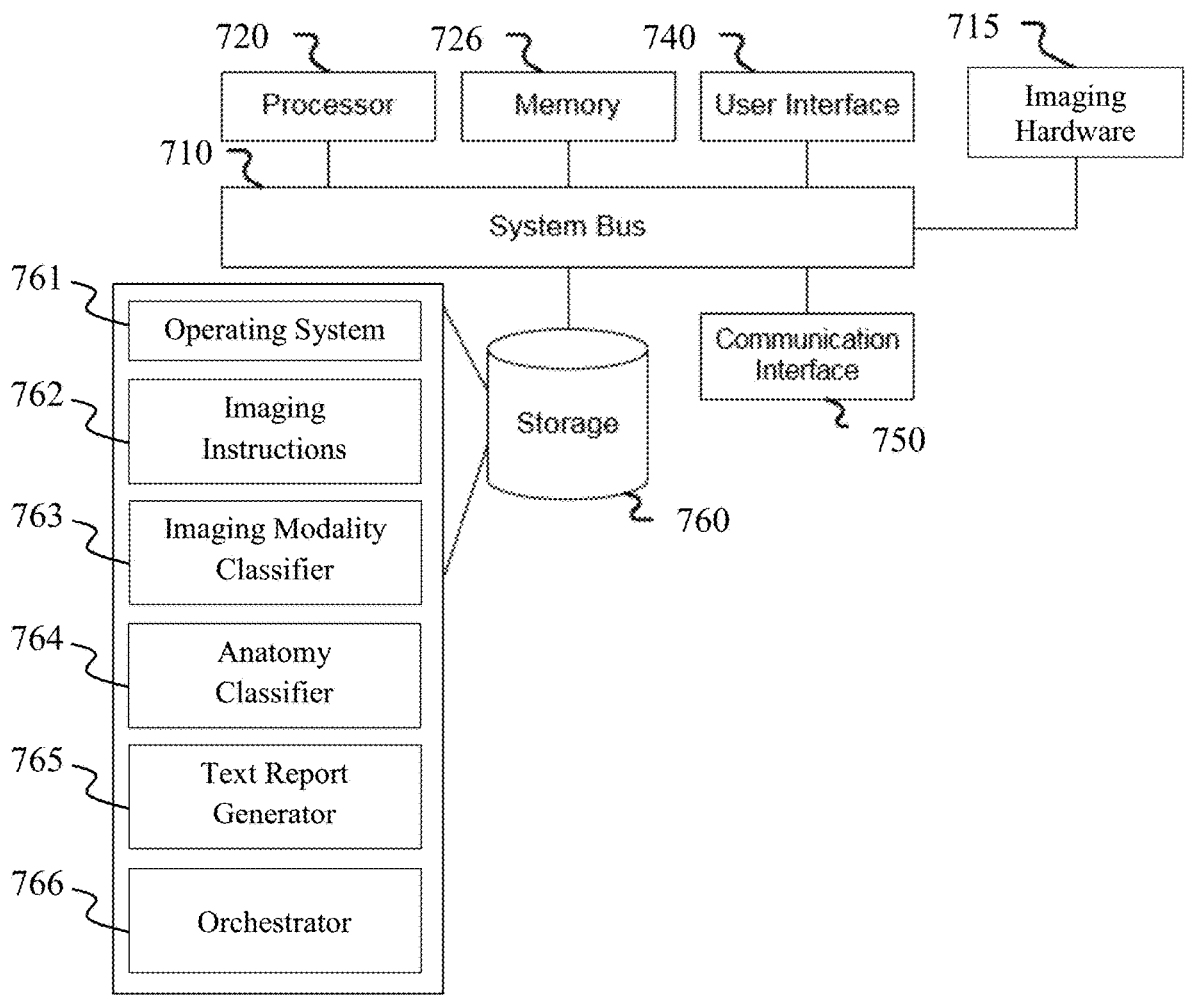
FIG. 7 is a schematic representation of models in a computer system architecture, in accordance with an embodiment.

Referring to FIG. 7, in one embodiment, is a schematic representation of a text generation system 700. System 700 can comprise any of the modules, elements, databases, processors, and/or other components described or otherwise envisioned herein. For example, the textual description generation system can comprise a processor having or in communication with an image modality classification module configured or programmed to differentiate between a plurality of different imaging modalities, an anatomy classification module configured or programmed to differentiate between specific portions of anatomy in an image, a text report generation module configured or programmed to generate a textual description based at least in part on information from a medical image, and/or an orchestrator module configured or programmed to transmit and/or receive data between the modules and to determine which of a plurality of different text generation models to utilize to generate a textual description from the medical image. System 700 includes one or more of a processor 720, memory 726, user interface 740, communications interface 750, and storage 760, interconnected via one or more system buses 710. In some embodiments, such as those where the system comprises or implements a medical imager, the hardware may include imaging hardware 715. It will be understood that FIG. 7 constitutes, in some respects, an abstraction and that the actual organization of the components of the system 700 may be different and more complex than illustrated.

According to an embodiment, system 700 comprises a processor 720 capable of executing instructions stored in memory 726 or storage 760 or otherwise processing data. Processor 720 performs one or more steps of the method, and may comprise one or more of the modules described or otherwise envisioned herein. Processor 720 may be formed of one or multiple modules, and can comprise, for example, a memory. Processor 720 may take any suitable form, including but not limited to a microprocessor, microcontroller, multiple microcontrollers, circuitry, field programmable gate array (FPGA), application-specific integrated circuit (ASIC), a single processor, or plural processors.

Memory 726 can take any suitable form, including a non-volatile memory and/or RAM. The memory 726 may include various memories such as, for example L1, L2, or L3 cache or system memory. As such, the memory 726 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of system 700. It will be apparent that, in embodiments where the processor implements one or more of the functions described herein in hardware, the software described as corresponding to such functionality in other embodiments may be omitted.

User interface 740 may include one or more devices for enabling communication with a user such as an administrator, technician, or clinician. The user interface can be any device or system that allows information to be conveyed and/or received, and may include a display, a mouse, and/or a keyboard for receiving user commands. In some embodiments, user interface 740 may include a command line interface or graphical user interface that may be presented to a remote terminal via communication interface 750. The user interface may be located with one or more other components of the system, or may located remote from the system and in communication via a wired and/or wireless communications network.

Communication interface 750 may include one or more devices for enabling communication with other hardware devices. For example, communication interface 750 may include a network interface card (NIC) configured to communicate according to the Ethernet protocol. Additionally, communication interface 750 may implement a TCP/IP stack for communication according to the TCP/IP protocols. Various alternative or additional hardware or configurations for communication interface 750 will be apparent.

Storage 760 may include one or more machine-readable storage media such as read-only memory (ROM), random-access memory (RAM), magnetic disk storage media, optical storage media, flash-memory devices, or similar storage media. In various embodiments, storage 760 may store instructions for execution by processor 720 or data upon which processor 720 may operate. For example, storage 760 may store an operating system 761 for controlling various operations of system 700. Where system 700 implements imaging hardware 715, storage 760 may include imaging instructions 762 for operating the imaging hardware 715. Storage 760 may also comprise one or more of an imaging modality classifier 763, an anatomy classifier 764, a text report generator 765, and/or an orchestrator 766. The storage 760 may store additional software components required to execute the functionality described herein, which also may control operations of hardware 700.

It will be apparent that various information described as stored in storage 760 may be additionally or alternatively stored in memory 726. In this respect, memory 726 may also be considered to constitute a storage device and storage 760 may be considered a memory. Various other arrangements will be apparent. Further, memory 726 and storage 760 may both be considered to be non-transitory machine-readable media. As used herein, the term non-transitory will be understood to exclude transitory signals but to include all forms of storage, including both volatile and non-volatile memories.

While system 700 is shown as including one of each described component, the various components may be duplicated in various embodiments. For example, processor 720 may include multiple microprocessors that are configured to independently execute the methods described herein or are configured to perform steps or subroutines of the methods described herein such that the multiple processors cooperate to achieve the functionality described herein. Further, where system 700 is implemented in a cloud computing system, the various hardware components may belong to separate physical systems. For example, processor 720 may include a first processor in a first server and a second processor in a second server.

According to an embodiment, system 700 stores, utilizes, and/or otherwise comprises one or more modules to carry out one or more functions or steps of the methods described or otherwise envisioned herein. For example, system 700 may comprise an imaging modality classifier 763, an anatomy classifier 764, a text report generator 765, and/or an orchestrator 766. According to an embodiment, imaging modality classifier 763 is trained to determine which of a plurality of possible imaging modalities were utilized to obtain a medical image. The imaging modality classifier 763 receives one or more medical images, such as from orchestrator 766, and analyzes one or more parameters, features, or other aspects of the received medical image to determine which imaging modality was utilized to obtain the received medical image.

According to an embodiment, system 700 stores, utilizes, and/or otherwise comprises an anatomy classifier 764 trained to determine which of a plurality of possible anatomies or structures are present in the received medical image. As described herein, the anatomy classifier can be trained to analyze the received medical image to distinguish between different anatomy, anatomies, or structures in medical images. According to an embodiment, the trained anatomy classifier analyzes one or more parameters, features, or other aspects of the received medical image to determine which anatomy is partially and/or completely contained within or otherwise represented by the image.

According to an embodiment, system 700 stores, utilizes, and/or otherwise comprises a text report generator 765 trained or configured to generate a textual description from the medical image. According to an embodiment, the system comprises a plurality of different text generation models each of which may function more efficiently and/or with higher accuracy for a specific image modality. Accordingly, the text generation system or other component of the system can be configured to select one or more of these models based on the determined image modality.

According to an embodiment, system 700 stores, utilizes, and/or otherwise comprises an orchestrator 766 trained or configured or programmed to transmit and/or receive data between the modules and to determine which of a plurality of different text generation models to utilize to generate a textual description from the medical image, among other functions.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for generating a textual description from a medical image, comprising:
   receiving the medical image, which was generated with a first modality of a system configured to generate the textual description of the medical image;
   determining, using an imaging modality classification module of the system, that the first modality is a specific one of a plurality of different modalities, wherein the imaging modality classification module is trained to differentiate between the plurality of different modalities;
   determining, using an anatomy classification module of the system, that the medical image comprises information about a specific portion of an anatomy, wherein the anatomy classification module is trained to differentiate between specific portions of anatomy;
   identifying, by an orchestrator module of the system based at least on the determined first modality, which of a plurality of different text generation models to utilize to generate a textual description from the medical image, wherein each of the plurality of different text generation models is utilized for a different modality;
   generating, by a text generation module of the system utilizing the identified text generation model, a textual description from the medical image, wherein the text generation module is trained to generate the textual description based at least in part on information from the medical image; and reporting, via a user interface of the system, the generated textual description.

2. The method of claim 1, further comprising the step of training, using a training data set comprising a plurality of medical images obtained using different imaging modalities, the imaging modality classification module to differentiate between a plurality of different imaging modalities.

3. The method of claim 2, wherein the plurality of different imaging modalities comprises at least CT scan, X-ray, MRI, PET scan, and ultrasound.

4. The method of claim 1, further comprising the step of training, using a training data set, the anatomy classification module to differentiate between a plurality of portions of anatomy.

5. The method of claim 1, further comprising the step of utilizing the reported textual description for diagnosis or treatment.

6. The method of claim 1, wherein the orchestrator module is configured to receive the medical image, and further configured to communicate the medical image to one or more of the imaging modality classification module, the anatomy classification module, and the text generation module.

7. The method of claim 1, wherein the step of reporting the generated textual description comprises providing both the generated textual description and displaying the medical image.

8. The method of claim 1, wherein one or more of the imaging modality classification module, the anatomy classification module, and the text generation module comprises a machine learning algorithm.

9. A system configured to generate a textual description from a medical image, comprising:
  an imaging modality classification module configured to receive a first medical image generated with a first image modality, and further configured to determine that the first modality is a specific one of a plurality of different modalities, wherein the imaging modality classification module is trained to differentiate between the plurality of different modalities;
  an anatomy classification module configured to determine an anatomy represented in the medical image, wherein the anatomy classification module is trained to differentiate between different anatomy in medical images;
  an orchestrator module configured to determine, based at least on the determined first modality, which of a plurality of different text generation models to utilize to generate a textual description from the medical image, wherein each of the plurality of different text generation models is utilized for a different modality;
  a text generation module configured to generate, utilizing the identified text generation model, a textual description from the medical image, wherein the text generation module is trained to generate the textual description based at least in part on information from the medical image; and
  a user interface configured to report the generated textual description.

10. The system of claim 9, further comprising imaging hardware configured to obtain the medical image using the first modality.

11. The system of claim 9, wherein the plurality of different imaging modalities comprises at least CT scan, X-ray, MRI, PET scan, and ultrasound.

12. The system of claim 9, wherein the orchestrator module is configured to receive the medical image, and further configured to communicate the medical image to one or more of the imaging modality classification module, the anatomy classification module, and the text generation module.

13. The system of claim 9, wherein one or more of the imaging modality classification module, the anatomy classification module, and the text generation module comprises a machine learning algorithm.

14. The system of claim 9, wherein the user interface is configured to report the generated textual description and to display the medical image.

15. The system of claim 9, wherein the user interface is configured to report the generated textual description to a clinician for diagnosis or treatment.

16. A non-transitory computer readable medium encoded with computer executable instructions, which when executed by a processor, cause the process to:
  receive a medical image generated with a first modality;
  determine that the first modality is a specific one of a plurality of different modalities;
  determine that the medical image comprises information about a specific portion of an anatomy;
  identify, based at least on the determined first modality, which of a plurality of different text generation models to utilize to generate a textual description from the medical image, wherein each of the plurality of different text generation models is utilized for a different modality;
  generate, utilizing the identified text generation model, a textual description from the medical image; and
  report the generated textual description.

17. The non-transitory computer readable medium of claim 16, wherein the instructions further cause the processor to train, using a training data set comprising a plurality of medical images obtained using different imaging modalities, the imaging modality classification module to differentiate between a plurality of different imaging modalities.

18. The non-transitory computer readable medium of claim 17, wherein the plurality of different imaging modalities comprises at least CT, X-ray, MRI, PET, and ultrasound.

19. The non-transitory computer readable medium of claim 16, wherein the instructions further cause the processor to train, using a training data set, the anatomy classification module to differentiate between a plurality of portions of anatomy.

20. The non-transitory computer readable medium of claim 16, wherein the instructions further cause the processor to utilize the reported textual description for diagnosis or treatment.

* * * * *